US006859516B2

(12) United States Patent
Schneider et al.

(10) Patent No.: US 6,859,516 B2
(45) Date of Patent: Feb. 22, 2005

(54) METHOD FOR EXAMINING STRUCTURES ON A SEMICONDUCTOR SUBSTRATE

(75) Inventors: Gerd Schneider, Bockenem-Bornum (DE); Bastian Niemann, Goettingen (DE); Dirk Hambach, Munich (DE)

(73) Assignee: Leica Microsystem Lithography GmbH, Jena (DE)

( * ) Notice: Subject to any disclaimer, the term of this patent is extended or adjusted under 35 U.S.C. 154(b) by 278 days.

(21) Appl. No.: 09/681,186

(22) Filed: Feb. 14, 2001

(65) Prior Publication Data

US 2001/0046276 A1 Nov. 29, 2001

Related U.S. Application Data

(60) Provisional application No. 60/182,375, filed on Feb. 14, 2000.

(51) Int. Cl.[7] .................................................. G21K 7/00
(52) U.S. Cl. .......................................... 378/43; 378/62
(58) Field of Search .............................. 378/58, 43, 62

(56) References Cited

U.S. PATENT DOCUMENTS

| 5,177,774 | A | * | 1/1993 | Suckewer et al. | 378/43 |
| 5,222,113 | A | * | 6/1993 | Thieme et al. | 378/43 |
| 5,434,901 | A | * | 7/1995 | Nagai et al. | 378/43 |
| 5,450,463 | A | * | 9/1995 | Iketaki | 378/43 |
| 5,533,083 | A | * | 7/1996 | Nagai et al. | 378/44 |
| 5,550,887 | A | * | 8/1996 | Schmal et al. | 378/43 |
| 5,703,361 | A | * | 12/1997 | Sartore | 250/310 |
| 6,163,590 | A | * | 12/2000 | Wilkins | 378/43 |

FOREIGN PATENT DOCUMENTS

| JP | 02-203261 | * | 8/1990 | .......... G01N/23/02 |

OTHER PUBLICATIONS

Schneider, Rontgenmikroskopie mit Synchrotronstrahlung an wassrigen biologischen Systemen—experimentelle und theoretische Untersuchungen, Dissertation, (1992), pps. 1–10.*
Schmahl et al., Proposal for a phase contrast microscope, X–ray microscopy Instrumentation and Biological Applications, Springer–Verlag (1987) ps. 231–238.*
Levine et al., Tomographic reconstruction of an integrated circuit interconnect, Applied Physics Letters, Jan. 4, 1999, vol. 74, No. 1, pps 150–152.*
Schneider, Cryo x–ray microscopy with high spatial resolution in amplitude and phase contrast, Ultramicroscopy 75 (1998), pps 85–104.*

(List continued on next page.)

*Primary Examiner*—Edward J. Glick
*Assistant Examiner*—Chih-Cheng Glen Kao
(74) *Attorney, Agent, or Firm*—Houston Eliseeva LLP (57) ABSTRACT

The invention is based on a method for examining structures on a semiconductor substrate. The structures are imaged with X-radiation in an X-ray microscope. The wavelength of the X-radiation is established as a function of the thickness of the semiconductor substrate in such a way that both a suitable transmission of the X-radiation through the semiconductor substrate and a high-contrast image are obtained. As a result, the structures can be observed continuously with short exposure times, high resolution and even while they are in operation.

15 Claims, 4 Drawing Sheets

OTHER PUBLICATIONS

Levine et al., *Tomographic reconstruction of an integrated circuit interconnect*, Applied Physics Letters, Jan. 4, 1999, vol. 74, No. 1, pps 150–152.*

Gerd Schneider, *Röntgenmikroskopie mit Synchrotronstrahlung an wässrigen biologischen Systemen—experimentelle und theoretische Untersuchungen*, Dissertation, zur Erlangung des Doktorgrades der Mathematisch—Naturwissenschaftlichen Fachbereiche der Georg–August–Universität zu Göttingen (1992), pp. 1–10 (US Translation of the relevant portions of the dissertation is provided).

B.L. Henke, et al., *X–ray Interactions: Photoabsorption, Scattering, Transmission, and Reflection at E=50–30,000 eV,Z=1–92*, Atomic Data And Nuclear Data Tables 54 (1993), pp. 181–183, 226, 241.

G. Schmahl, et al., *Proposal for A Phase Contrast Microscope*, X–ray Microscopy Instrumentation and Biological Applications, Springer–Verlag(1987), pp. 231–238.

Gerd Schneider, *Cryo X–ray microscopy with high spatial resolution in amplitude and phase contrast*, Ultramicroscopy 75 (1998), pp. 85–104.

* cited by examiner

METHOD FOR EXAMINING STRUCTURES ON A SEMICONDUCTOR SUBSTRATE

CROSS REFERENCE TO RELATED APPLICATIONS

This application claims priority from an earlier filed U.S. Provisional patent application Ser. No. 60/182,375 filed Feb. 14, 2000, which is incorporated herein by reference

BACKGROUND OF INVENTION

The invention concerns a method for examining structures on a semiconductor substrate. The structures can be, in particular, operable integrated and nonintegrated electronic circuits in the micrometer and nanometer range, or micromechanical components in the micrometer and nanometer range.

The structures of semiconductor elements, for example memory modules, microprocessors, and logic modules, are manufactured on a semiconductor substrate, called a "wafer," that generally comprises a silicon single crystal and usually has a thickness of between 200 and 600 $\mu$m. There are also special wafers having very thin semiconductor substrates, whose thicknesses are much less than 100 $\mu$m.

Semiconductor components, which are located in layers a few micrometers thick that are very close to the surface and whose structures can have lateral extensions of, at present, approximately 200 nm or less, are produced on such wafers using lithography and coating and doping methods. In order to manufacture a usable semiconductor chip therefrom, the structures produced in this fashion must be equipped with electrical leads, which in turn can be generated by lithography. The leads generally are made of metals such as, for example, copper or aluminum. Tungsten and tantalum are also used. To allow such conductor paths to cross one another without electrical short-circuiting, intermediate steps are used to apply electrically insulating intermediate layers whose lateral extension and shape can once again be dimensioned very accurately using lithography. Later, once again using various methods, electrical connections must then be produced in the vertical direction; these create contact, through the insulator, between leads or doped zones of one plane and the leads of the other plane. The result is thus a three-dimensional conformation of semiconducting, conducting, and insulating structures, which must be accurately coordinated with one another in terms of their spatial positions.

If defects occur in such structures, they must be examined. This is done, for example, with microscopes. Light microscopes, scanning electron microscopes, atomic force microscopes (AFMs), and acoustic microscopes can be used.

A disadvantage of optical microscopes in this context is that these microscopes are operating close to their resolution limit, since the size of the structures being examined and the light wavelength (which physically limits the resolution of a microscope) are approximately equal in size.

Attempts are occasionally made, for example, to examine the adhesion of electronic structures to the substrate using acoustic microscopes, exploiting the different reflectivity of the sound waves at such defect sites. Once again, however, the limited resolution of the acoustic microscopes constitutes an impediment.

Other examinations can be made with an electron microscope if the structures being examined are first exposed, for example, by chemically removing the substrate that carries the structures. A method of this kind is thus not nondestructive, and requires careful preparation of the layered structures that are to be exposed. In addition, the radiation election beam of an electron microscope can pass through only very thin layers, and three-dimensional tomographic reconstruction of more deeply extending structures is not possible.

Modern computer chips contain a large number of transistors, which are connected to one another by fine wires (called "conductor paths") made of aluminum. If a chip of this kind is viewed under a light microscope at sufficient magnification, it is even possible to recognize grain boundaries in these conductor paths.

The conductor paths in modern microelectronic components can carry very high current densities ($10^6$ A/cm$^2$ and more) without excessive heating, since they are effectively cooled by being embedded into the surrounding silicon or dielectric layers. The current densities are so high that many electrons strike the atoms directly, and can physically displace them in the direction of current flow; this effect is called "electromigration," and can result in damage to or destruction of the conductor paths.

Since the atoms in grain boundaries or in interfaces between the metal of the conductor paths and surrounding materials can move particularly easily, it may happen that holes form at certain locations due to the high level of material transport, and that at other locations material is pushed out of the conductor path. Either can result in breakdown of the conductor path and thus failure of the entire chip. In the foreseeable future this effect could limit the further miniaturization of computer chips, and materials scientists throughout the world are therefore working very intensively on this problem.

Electromigration in conductor paths is one of the principal causes of the failure of integrated circuits, and because of the ever-increasing integration of such circuits it continues to be a major problem. To study the service life of conductor path metallizations, highly accelerated tests are performed under exaggerated stress conditions, such as elevated current density and elevated temperature. Unpassivated conductor paths are often used to study the migration processes, since they allow better microscopic examination of the failure sites with particularly high spatial resolution. Omission of the passivation applied over the conductor paths—i.e. the protective insulation layers made of, for example, $SiO_2$, $Si_3N_4$, or plastic that are applied over the conductor paths—generally causes a change in the way the electromigration processes occur. These changes have to do with material transport and thus with local volume changes, by way of which the pressure and temperature conditions in the vicinity of the conductor path are influenced by the passivation layers. Unpassivated conductor paths, in which the overlying insulation layers are absent, therefore generally behave (e.g. in terms of electromigration) slightly differently from the passivated components used in practice.

The need, therefore, exists for an imaging method that permits high spatial resolution even when the structures to be examined lie under dielectric materials several $\mu$m thick. The resolution achievable with microscopes for visible light is often too low. With transmission electron microscopes, high-resolution images can be obtained only of layers up to a maximum of 1 $\mu$m thick. Surface-sensitive methods such as atomic force microscopy (AFM) or secondary electron microscopy (SEM) either require destructive specimen preparation or achieve only poor resolution as a result of electron scattering in thick passivation layers. Atomic force microscopes have an additional disadvantage that they are scanning systems and thus require relatively long examination times, and, therefore cannot produce real-time images for continuous observation.

In principle, it is also possible to examine thin metal structures with an X-ray microscope. X-ray microscopes operate in the wavelength region below a maximum of 20 nm. Since the maximum possible resolution of a microscope is in the order of half the wavelength, it is possible to achieve much higher resolution with an X-ray microscope than with a microscope using visible light or UV radiation. In general, the shorter the wavelength of the X-radiation used and the thinner the specimen, the greater the ability of the radiation to penetrate through a specimens.

Depending on the wavelength, X-radiation is in some cases considerably attenuated even in the air under standard conditions. Because X-ray microscopes usually have an overall length of several meters, in order to prevent unnecessary losses of radiation through absorption, the radiation always propagates through evacuated chambers until reaching an area close to the specimen. There the radiation passes through a thin window—made, for example, of a thin but pressure-resistant film—into the air under standard conditions, in which the specimen is also located. Placed behind the sample is usually another window into another evacuated chamber in which the imaging X-ray objective is located, and in which the X-radiation is directed to the X-ray detector. The specimen can also, however, be surrounded by a sealable chamber that is filled with an inert gas or evacuated.

The only high-resolution X-ray objectives used today in X-ray microscopes for wavelengths less than 20 nm are zone plates, since only they can provide sufficiently high resolution. They must be operated with monochromatic radiation, however, since the focal length is inversely proportional to wavelength.

X-ray sources for X-ray microscopes are, for example, deflector magnets, wigglers, or undulators of electron-beam storage rings. The radiation from undulators is quasi-monochromatic (wavelength as a function of bandwidth $\delta\lambda$, i.e. $\lambda/\delta\lambda$, is approximately 100), and is thus directly suitable for X-ray microscopes using zone plates with a very small number of zones (typically 100 zones) as their X-ray objectives; if zone plates with a greater number of zones are used, or if the radiation sources are wigglers or deflector magnets, the X-radiation must in any case also be monochromatized.

In the wavelength region below 20 nm, X-ray microscopes can be operated in amplitude contrast and in phase contrast. Phase contrast is particularly suitable below 2 nm, since it produces much higher contrast than amplitude contrast. This has to do with the optical constants of the refractive index for X-radiation, which are favorable for phase contrast in this wavelength region.

There are two important types of X-ray microscopes: imaging and scanning X-ray microscopes. Imaging X-ray microscopes produce a real image that can be recorded with a camera. To allow an imaging X-ray microscope to operate in phase contrast, a phase plate with an appropriate phase shift must be arranged in the back focal plane of the zone plate used for imaging. Further details of phase contrast have been described in the technical literature.

Scanning X-ray microscopes generate an image by a serial process in which radiation passes through a specimen one point at a time, and an image is generated on a monitor. Because of this serial image recording performed one point at a time, long examination times are necessary, so that continuous observation of a specimen is not possible. Image creation times are within a range of 100 to 1000 seconds. A scanning X-ray microscope of this kind for three-dimensional tomographic reconstruction of a metal connection in an integrated circuit is known from the article by Zachary H. Levine, Andrew R. Kakulin, Sean P. Frigo, Ian McNulty, and Markus Kuhn: "Tomographic reconstruction of an integrated circuit connect," Applied Physics Letters, Vol. 74, No. 1, pp. 150–152, Jan. 4, 1999. The thickness of the substrate was thinned to a few $\mu$m for the examination.

SUMMARY OF INVENTION

It is the object of the invention to describe a method and an apparatus for the examination of structures, in particular functional structures, on semiconductor substrates, with which the structures can be observed with little destruction, with short exposure times, continuously, even while they are in operation, and with a better resolution as compared to optical microscope, in which context the structures do not need to be detached from the substrate.

This object is achieved by the features of independent claims. Advantageous developments of the method and the apparatus are evident from the corresponding dependent claims.

According to the invention, an imaging X-ray microscope is used for examination of the structures on a semiconductor substrate. X-radiation is passed through the structures, and they are imaged on a spatially resolving detector. Suitable wavelengths of the X-radiation are set, as a function of the thickness of the semiconductor substrate, so as to achieve both sufficient transmission of the X-radiation through the semiconductor substrate to allow detection of the X-radiation, and a high-contrast image. With many specimens, the substrate thicknesses are already thin enough for this purpose. In all other cases the substrate thicknesses must be correspondingly reduced, for example, by etching.

If the substrate is made, in particular, of silicon, then the X-radiation is preferably set to the wavelengths between 2 nm and 0.1 nm, and the thickness of the silicon wafer should preferably be between 10 $\mu$m and 30 $\mu$m.

At greater substrate thicknesses, in particular thicknesses exceeding 100 $\mu$m, radiation absorption by the silicon substrate is so great that the radiation is almost completely absorbed within it, which would result in very long exposure times for the X-ray microscopic image. Wafers having such substrate thicknesses are therefore correspondingly thinned without altering the functionality of the structures. If the structures are located on only one side of the silicon substrate, and if the other side has no structures (as is the case with most substrates), then the substrate can be thinned from the structure-free back side.

In the case of wafers on which electrical circuits are integrated, the structures comprise active conductor path layer systems and doped regions. They represent the electronic components on the wafer. Their electrical functionality is not restricted by any thinning, since the electronic components extend to depths of only a few micrometers and a sufficient substrate thickness still remains even when the substrate is thinned.

On substrates and especially on silicon wafers, micromechanical structures can also be applied onto or into the surface of the substrate. Such micromechanical structures can be, for example, the membranes of a pressure sensor, movable structures of an acceleration sensor, or micromechanical gears or pumps. Structures of this kind can also be examined with the method according to the present invention.

Suitable substrates include all materials on which and with which the desired structures can be produced. Silicon is particularly suitable for microelectronic circuits and also for micromechanical components, but all other crystals that can be doped for semiconductor modules (e.g. gallium arsenide), are also usable.

With the optionally thinned semiconductor substrates and the use of imaging X-ray microscopes, and with the X-radiation wavelengths adjusted for the substrate thickness, exposure times of the order of 1 second are achieved. This makes it possible to produce real-time images of the structures on the substrates, which can be observed continuously while they are in operation.

An advantage of the method according to the present invention is that the structures do not need to be destroyed, as is necessary with many other methods in which the upper layers of the structures must be removed, mechanically or by etching, so that the structures lying below them can be made visible and can be examined, for example, with an optical microscope. The selected X-radiation and the imaging X-ray microscope according to the invention make it possible to examine complete, operable structures, and in particular, their size and relative position. Additionally, because imaging occurs continuously in real time, the operable structures can also be observed while they are in fact operating, so that movements of the structures or any structural changes in the micromechanical or electronic structures can be followed over time.

In general, X-radiation is always associated with a certain radiation damage to materials. It is therefore advantageous if the structure-free side of the substrate is exposed first to the incident X-radiation, so that the substrate first absorbs some of the radiation. The exposure time—and thus, indirectly, also the radiation damage to the functional elements present on the substrate—is minimized by careful selection of the wavelength based on a calculation of the X-ray-optical transmission of the substrate and the scattering characteristics of the structures present thereon that are to be examined.

The method allows fully functional circuits on wafers to be examined, even while they are operating, with a resolution greater than that of visible light. This can occur under a wide range of parameters and external influences; for example, migration processes in passivated conductor paths can be studied, and a three-dimensional depiction is becomes possible by tomographic reconstruction of X-ray microscope images. This requires that the specimen be imaged at a plurality of different tilt angles.

Changes in material distribution resulting from electromigration processes can be studied. It is thus possible to do so even with the technologically relevant passivated conductor paths usually used in commercial integrated circuits, and to compare the examination results to model calculations. This means that better data are obtained for the simulation and development of integrated circuits.

In very general terms, all radiation sources that generate intense X-radiation in the wavelength region between 2 and 0.1 nm are suitable for examination of the structures; ideally, in order to allow for as many of the applications as possible, which will be described below, such sources preferably should not emit only one specific line radiation of fixed wavelength.

X-ray microscopes having zone plates are preferably operated with monochromatic radiation, since zone plates exhibit chromatic aberration. However, this is not a fundamental disadvantage of the method described in more detail below, since some of the methods described below call for monochromatic X-radiation.

Monochromatization can be accomplished, for example, with a monochromator that can also be a constituent of the condenser in the microscope. The X-radiation sources can also furnish linearly or circularly polarized radiation, which is already being used for examination of the "circular magnetic dichroism" of ferromagnetic materials.

Since undulators emit X-radiation quasi-monochromatically and the frequency of wavelengths can vary, it is possible to select any desired center X-ray wavelength in the aforementioned wavelength region. The monochromatic nature of the radiation can then be further enhanced by means of suitable monochromators, if necessary for the examinations (see below), so that in measurements using wavelengths at the absorption discontinuities, their slight discontinuity displacements can be used to produce image contrast.

At a wavelength of 1 nm, zone plates for X-radiation typically have a focal length of a few mm; the object distance is then somewhat greater, in accordance with the conjugate distance equation, depending on the X-ray magnification. The resolution of presently available zone plates is 50 nm for this wavelength region; it is thus considerably better than that of a microscope for visible light or UV radiation. At a wavelength of 0.1 nm the focal length for a given zone plate objective is 10 times greater, since the focal length increases as the reciprocal of the wavelength.

What is essential for any examination of semiconductor chips is that they possess sufficiently high X-ray transmittance. If X-ray microscopes are operated with X-ray wavelengths in the region less than 2 nm, it is already possible to penetrate through layers several micrometers thick. The exact value depends on the material being penetrated. For silicon, the typical substrate material for semiconductor chips, the 1/e thickness (at which penetration still occurs with 37% transmission) is 4.8 $\mu$m at an X-ray wavelength of 1 nm and 33.3 $\mu$m at 0.2 nm. Thin substrate layers of this kind can be produced by treating the chip that is to be examined after the fact, with standard commercially available semiconductor components, from its back side, an etching substance, such as a chemically active fluid (e.g. ethylenediamine, KOH, or mixtures of hydrofluoric acid, acetic acid, and nitric acid) or can be used for etching, reactive dry etching in an etching facility in which reactive ions are present can be used for thinning the substrate, or neutral or charged inert-gas atoms can be used for etching.

The side containing electronic structures can be easily protected from etching, by being coated with wax, which is then dissolved after etching. Other organic materials can also be used for the protective layer, provided they can be later removed with solvents without damaging the electronic circuits. It is also possible to prevent the agent used for etching from acting on the electronic structures by placing the substrate that is to be thinned on top of a cup as a sealing cover, so that the side to be thinned ends up on the outside or inside, depending on whether etching is to occur from the inside or outside, respectively. It is furthermore possible to thin such layers by way of chemically assisted mechanical grinding.

As a semiconductor chip of this kind is being thinned, the simplest way to monitor the remaining thickness is to illuminate the semiconductor chip from one side with visible light, and on the other side to monitor the transmission of light, for example, visually or by measuring it with a light-sensitive electrical measurement instrument.

As soon as the thickness of about 10 µm is reached, silicon becomes perceptibly optically transparent, and thinning must be stopped so as not to damage the very structures being examined and their functionality. This thickness is thin enough to be penetrated by X-radiation at wavelengths shorter than 2 nm during very short exposure times.

At a given layer thickness and X-ray wavelength, each material has a different transmittance. Since X-ray transmittance generally increases with decreasing atomic number of a chemical element, carbon exhibits a much higher transmittance than, for example, silicon in the wavelength region between 2 nm and 0.1 nm. If a plastic is therefore used as the airtight protective coating on the side containing electrical structures (passivation of the structures), it has almost no negative effect on transmittance in the wavelength region below 2 nm if its thickness is approximately 10 µm or less. Thinning of these plastic coatings is therefore generally not necessary.

In some cases the semiconductor modules are already present in thinned form even in their commercial version (e.g. in the case of memory modules). Such modules can be examined directly (after removing any sheathing that may be present) without further thinning, with short exposure times for the X-ray microscopic images.

The semiconductor chip (thinned, if applicable) is then placed in the specimen holder of an X-ray microscope and imaged in transmitted radiation at a wavelength that must be carefully selected. At the wavelengths in the range between 0.1 and 2 nm that are used, high-resolution zone plate objectives typically have depths of field in the range of 10 µm and more, which is substantially greater than the thickness of the conductor paths and doped regions of semiconductor chips (and in some circumstances may be greater than the substrate thickness of the semiconductor chip).

The object distances achieved under these conditions can be up to one centimeter or more, which even allows a specimen under examination to be tilted in order to produce X-ray transmission images at different angles, for example, in order to obtain images for stereo viewing. If an entire series of images is taken at different angles using X-ray objectives with a long depth of field, it is possible to use digital tomographic reconstruction means to determine the three-dimensional configuration of the semiconductor chip structures by calculation.

Since metals such as aluminum, copper, tungsten, and tantalum exhibit absorption discontinuities in the wavelength region between 0.1 and 2 nm, there is a great change in image contrast when X-ray images are made at wavelengths preceding and following the corresponding absorption discontinuity. This is possible because at the absorption discontinuity of an element, its absorption and phase shift can change almost abruptly. By taking images close to the absorption discontinuities, it is thus possible to record the specific spatial distribution of the corresponding material.

The examination of functional semiconductor chips in an X-ray microscope offers even more advantages. Since the radiation passes through all structures and also reveals whatever covers them, the result is a visual impression which corresponds to that of a conventional medical X-ray image. If the substrate is imaged without tilting—i.e. with the substrate surface perpendicular to the direction of the X-radiation—it is then possible to assess, with a single image at a relatively short exposure time, how the semiconductor chip structures overlap one another and whether they are correctly aligned laterally with respect to one another. In addition, the patterning quality can be checked directly in terms of line width, edge roughness, and layer thickness uniformity. Impurities can also be detected.

The semiconductor chip can be located in air, in the inert gas atmosphere, or in a vacuum. A variety of examinations, in particularly, electronic tests, can be performed during X-ray microscopic observation. It is possible, for example, to observe the transport of conductor path material in response to current flow (electromigration). In principle, measurements can be performed over a wide temperature range, from several hundred degrees Celsius down to the temperature of liquid helium; at temperatures below ambient, the environment around the specimen must be flushed with an anhydrous gas (e.g. $N_2$) to prevent water from freezing onto the specimen, or the specimen chamber containing the specimen can be vacuum created.

Measurements of semiconductor chip structures at elevated temperatures make it possible to accelerate aging processes up, for example, a few hours, by heating a substrate with semiconductor chip structures to a high temperature. Relevant changes that need to be observed, such as conductor path breaks, can then occur within a few seconds. With the method and apparatus according to the present invention, it is possible to observe this event in real time and with high precision and precisely. It is known that the material distribution on the substrate can change as a result of diffusion or electromigration processes. This change in the material distribution results in a change in image contrast, and can be observed under an imaging X-ray microscope.

X-ray microscope images can be made during the flow of current through functional structures. If the current that is flowing is greater than is permissible, it is possible to observe the points at which the structures are greatly modified or indeed destroyed, so that electrical voids or short-circuits are caused. Because of the change in material distribution, this process is visible as a change in the X-ray contrast of the image.

It is possible to make X-ray microscope images in which defects, thin spots in conductor paths, dust particles, and voids in conductor paths can be discovered.

X-ray microscope images can be captured while the current is flowing through the semiconductor circuit, revealing a change in image contrast in real time. The change can be explained by the fact that the applied electrical voltage changes the electron density distribution, which in turn has the feedback effects on the inner-shell electrons and thus results in a shift in the energy of the absorption discontinuities and a change in fine-scale structure. For this purpose, the microscope must be operated with highly monochromatic X-radiation, which can be generated, for example, by adding an upstream crystal lattice monochromator. The X-ray image is It is then used to locate those areas in the electronic structures where the current flow in the semiconductor chip is concentrated.

All these observations are in principle also possible with a scanning X-ray microscope, both in pure amplitude contrast and in pure phase contrast—i.e. with a +90° (or 90°) phase rotation of the zero-order diffraction of the specimen X-ray light in the phase plate—and in "optimized phase contrast." In optimized phase contrast, the thickness of the phase plate is selected so that for a predefined signal-to-noise ratio, a given specimen can be imaged with a minimum number of photons, thus resulting in particularly short exposure times. This is important for continuous observation of processes in semiconductor chips over time, so that the shortest possible exposure times can be achieved. The result is generally a phase plate for which the phase shift is not equal to 0°, 90°, 180°, and 270°.

When a scanning X-ray microscope is operated with high-energy radiation, X-ray fluorescence radiation can be generated from all those chemical elements having absorption gaps with energies lower than that of the exciting radiation. Simultaneously, the scanning X-ray microscope transmission signal can be observed. Using a photon energy-selective detector placed behind the specimen, it is thus possible to detect signals from different elements simultaneously as a function of the location of the scanning X-ray spot on the specimen. This can be done quantitatively and with sufficient selectivity, for example, to make the p- and n-doped regions of a semiconductor visible. This is also important, for example, when observing the artificial aging processes already discussed above, and the electromigration phenomenon already mentioned.

Both microscope types (imaging and scanning X-ray microscopes) also make possible any kind of X-ray microscopy examination of the specimens that does not interfere, for example due to excessive absorption, with propagation of the X-radiation through the specimen chamber (i.e. the volume that is at atmospheric pressure or in the inert gas atmosphere or vacuum) in which the specimen is located.

In particular, the specimen can be exposed to external electrical and magnetic fields; it can be irradiated with light or radiation of any desired wavelength; and it can be exposed to ion beams or electron beams and to elevated pressure or mechanical stresses.

The aforesaid examinations using the X-ray microscope can, of course, also be performed on nanostructures of similar configuration, for example micromechanical components or photonic crystals.

BRIEF DESCRIPTION OF DRAWINGS

The invention will be explained in more detail below with reference to the exemplary embodiments depicted in the drawings, in which, schematically in each case.

DETAILED DESCRIPTION

Figure 1:
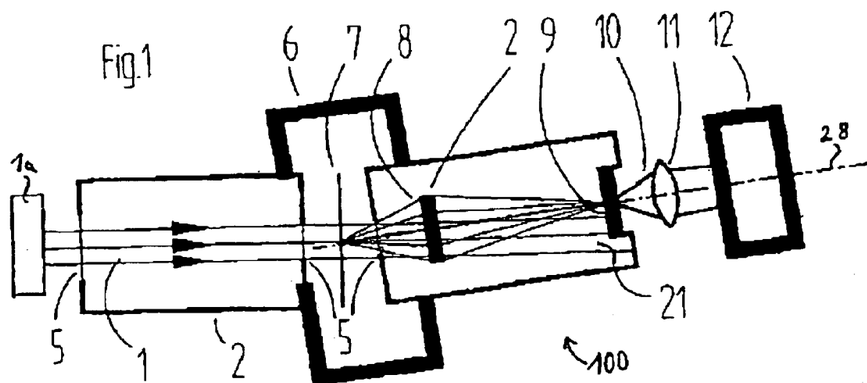
FIG. 1 shows an imaging X-ray microscope having an X-ray objective (but no condenser) for recording a real image, taken with a detector device having a camera, of a specimen being examined.

FIG. 1 schematically shows an X-ray microscope 100 that operates without a condenser. This means that X-radiation 1 generated by an X-ray source 1a (e.g. an electron storage ring) impinges upon specimen 7 under examination without further focusing. Specimen 7 is a semiconductor substrate which has micromechanical or electronic structures that are to be examined. As shown in FIG. 1, X-radiation 1 passes through a vacuum chamber 2, sealed vacuum-tight with X-ray windows 5, in which vacuum prevents absorption of the X-radiation. Radiation 1, propagating along a straight line, illuminates specimen 7 which is located, in air, in a specimen chamber 6.

An imaging objective 8 images a region of specimen 7 onto an X-ray converter 9, which converts the X-radiation into an optical radiation 10 that usually lies in the visible wavelength region. Optical radiation 10 is imaged through a lens 11 by a camera 12. X-ray converter 9, lens 11, and camera 12 thus form a detector device for the X-radiation. A detector device of this kind can, however, also comprise only a single directly illuminated detector, for example a PN-CCD detector, which is arranged in X-ray microscope 100 in place of X-ray converter 9. These different types of detectors for the X-radiation are usable for all X-ray microscopes 100 shown in the FIGS.

If imaging objective 8 comprises a diffracting optical system such as, for example, a zone plate (and not a refracting optical system as described below), the image field located in the straight-ahead direction cannot be used, since a strong zero-order radiation 21 that interferes with the image would at that point be superimposed on the image and decrease contrast. In this case an image must be created with oblique illumination, so that the image and the interfering zero-order radiation 21 lie next to one another. For that purpose, optical axis 28 of X-ray microscope 100 is tilted relative to the irradiation direction of the illuminating X-ray wave, thus, creating an oblique illumination.

Especially when elements of similar atomic number need to be distinguished from one another in the X-ray image, it may be necessary to minimize the photon density in specimen 7 necessary for imaging, since structures comprising elements with atomic numbers disposed next to or above each other can generate particularly low image contrast. The goal in this context is to determine the wavelength at which the photon density necessary for imaging reaches a minimum, so that with the minimized photon density, the maximum signal-to-noise ratio can be achieved in the image.

The minimal photon density can be determined, for example, by calculating the Rayleigh-Gans scattering cross section (cf., for example, G. Schneider, Dissertation, University of Göttingen, 1992, and Gerd Schneider, "Cryo X-ray microscopy with high spatial resolution in amplitude and phase contrast" in Ultramicroscopy 75 (1998) pp. 85104, the teachings of which are incorporated herein by reference. The minimal photon density is calculated there by using Equation 31). If this scattering cross section is zero, then the specimen cannot be imaged. This scattering cross section is a general indication of the radiation scattering capability of fine structures. For the X-ray wavelengths the scattering cross-section is a function of the atomic scattering factors f1 and f2, the wavelength, and the specimen size. The atomic scattering factors f1 and f2 are tabulated in B. L. Henke et al. (B. L. Henke, E. M. Gullikson, and J. C. Davis, X-ray interactions, photoabsorption, scattering, transmission and reflection. E=5030,000 eV, Z=192, Atomic Data and Nuclear Data Tables, 27, pp. 1144, (1982)), the teachings of which are incorporated therein by reference.

The photon density required for imaging in X-ray microscope 100 scales reaches a minimum at the wavelength at which the scattering cross section reaches a maximum, because the photon density is inversely proportional to the scattering cross section. The transmittance of the substrate additionally needs to be taken into account; in other words, in order ultimately to be able to determine the requisite photon density and thus the optimum wavelength for imaging a structure, the reciprocal of the scattering cross section must be multiplied by the reciprocal of the substrate transmittance. With this procedure, the wavelength region for imaging specific structures within a layer system can then be optimized in terms of the necessary photon density.

Proceeding from the photon density calculation, it is also possible to calculate and minimize the radiation dose of one wavelength absorbed by the structures, in order to suppress to the greatest extent possible any radiation effects on the structures. The minimum dose for the structures under consideration here is proportional to the linear absorption coefficient of the material, the quantum energy of the X-ray photons, the reciprocal of the scattering cross section, and the reciprocal of the density of the material in question. In order for this proportionality to be valid, it is necessary for the thickness of the structures at the X-ray wavelength used for examination to be less than their 1/e thickness (at which the structures still possess 37% X-ray transmittance). This condition does indeed exist for the materials under consideration here and for their thickness in conductor paths. In the interest of minimizing the dose that is absorbed by the structures in question, the thinned side of the substrate should always be placed into the X-ray microscope facing toward the source. The beam is then already weakened as it passes through the wafer crystal on its way to the structures of interest, and irradiates the structures with less intensity than it would be the case if the structures were located on the side that faces toward the radiation source.

In order to calculate the photon density and minimum dose for imaging in a) amplitude contrast, b) pure phase contrast, and c) a combination of amplitude and phase contrast (which utilizes both the phase rotation and the absorption in the specimen to create an image), these three instances can be simulated by a) setting the real portion of the complex atomic scattering factor at zero, b) setting the imaginary portion of the complex atomic scattering factor at zero, and c) not changing either of the two atomic scattering factors, i.e. by using the tabulated values of B. L. Henke et al. from "Atomic Data and Nuclear Data Tables" (see above).

The aforementioned deflector magnets, wigglers, and undulators of an electron beam storage ring are sources of intense X-rays, and supply a high flux of X-radiation. Nevertheless, the number of photons available per second is always a factor limiting the image recording time. It is therefore advisable to operate the X-ray microscope in phase contrast. The phase shift of the phase plate should be such that the microscope analyzes both the amplitude attenuation and phase rotation in order to record the image. The number of photons necessary to produce an image can be minimized if the phase plate possesses a very specific transmittance and phase rotation, to be individually determined for the particular wavelength and the material of the structure being examined. In general, phase rotations not equal to +90° or 90° are necessary. The criterion here is to achieve the best signal-to-noise ratio with a minimum number of photons. Programs for this purpose may be found in the literature (Gerd Schneider, "Cryo X-ray microscopy with high spatial resolution in amplitude and phase contrast" in Ultramicroscopy 75 (1988), pp. 85–104, the teachings of which are incorporated herein by reference).

In the case of an imaging X-ray microscope, phase contrast imaging is achieved using a phase ring that is placed in the back focal plane of the X-ray objective (G. Schmahl et al.) In the case of a scanning X-ray microscope, structures on semiconductor substrates can also be examined using phase contrast arrangements which are described here for the first time, and indeed even using arrangements without real phase rings.

Figure 2A:
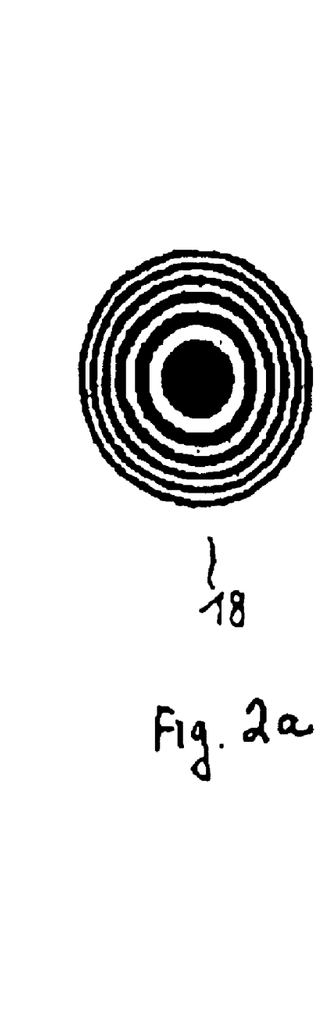
FIG. 2a shows a zone plate.

FIG. 2a shows in plain view a zone plate that represents a radially symmetrical circular grating having a grating constant that decreases toward the outside. The light-colored zone rings are transparent to X-radiation. The zones shown as dark in FIG. 2a are made either of a material that absorbs X-radiation (in which case the term "absorption zone plate" or "amplitude zone plate" is used), or of a material that creates a particularly strong shift in the phase of the X-radiation and possesses little absorption (the term then being "phase zone plate"). Zone plates with very small structures are also called "micro-zone plates" and are used, among other purposes, as X-ray objectives 8 and condensers 3.

Figure 2B:
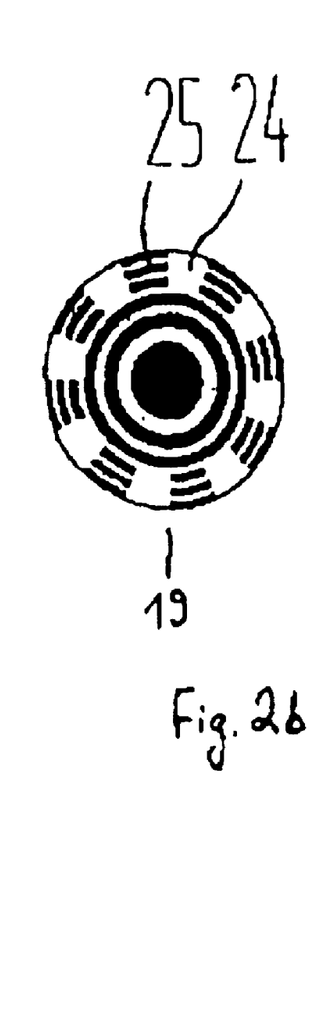
FIG. 2b shows a condenser zone plate with outer segments that have no zone structures.
Figure 2C:
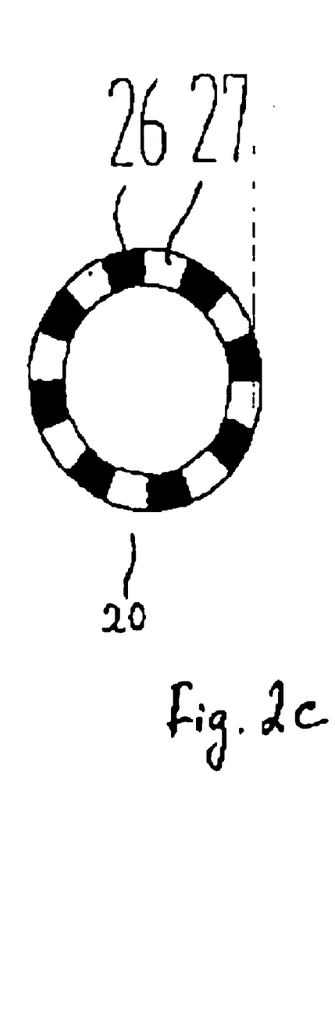
FIG. 2c shows a segmented phase ring.
Figure 2D:
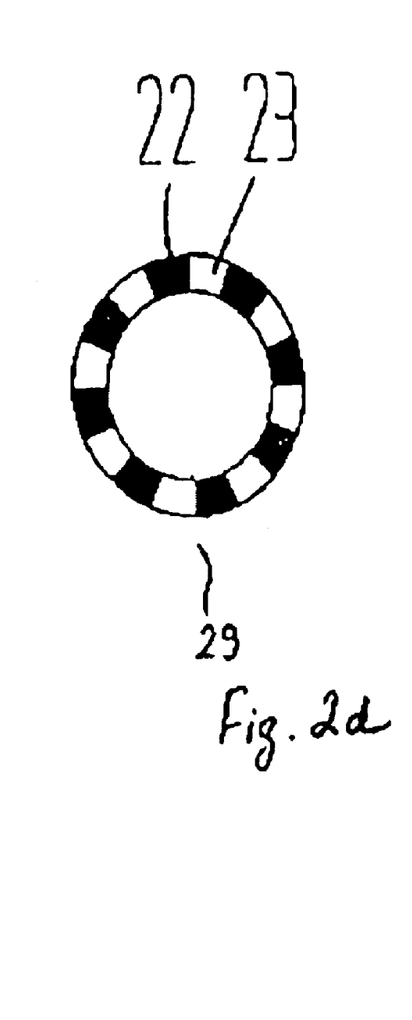
FIG. 2d shows a segmented stop.

FIGS. 2b through 2d will be described in conjunction with the descriptions below of the further Figures.

Figure 3:
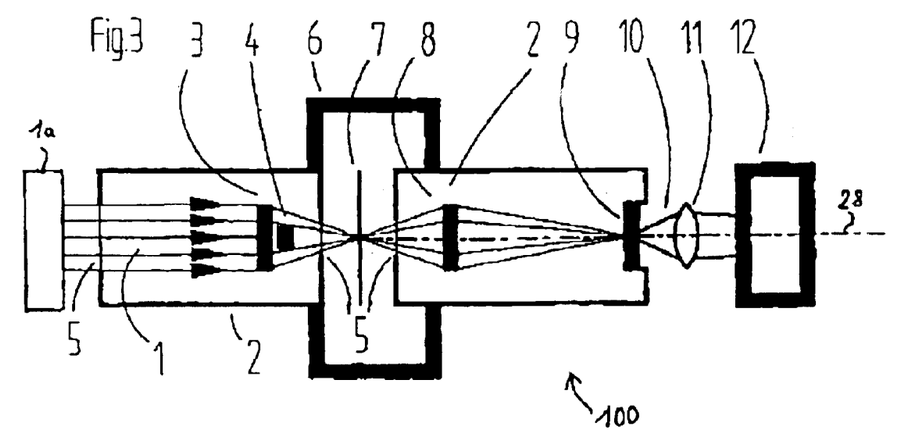
FIG. 3 shows an X-ray microscope having an X-ray condenser, an X-ray objective, and a detector device having a camera.
Figure 3A:
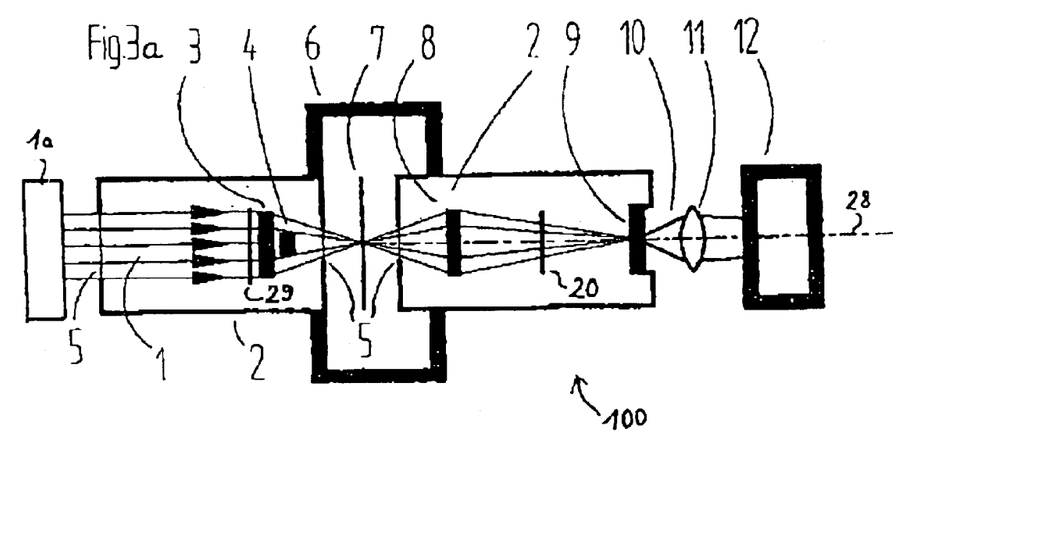
FIG. 3a shows an X-ray microscope according to FIG. 3 additionally having a phase plate and a stop.

As shown in FIG. 3, specimen 7 is illuminated using an X-ray condenser 3. A radiation-opaque stop 4 arranged in the center of the resulting cone of rays brings about hollow-cone illumination of specimen 7. To allow a rapid switchover from amplitude contrast to phase contrast with an imaging microscope as shown in FIG. 3 using hollow-cone illumination, or in order to make the phase angle of the phase contrast arrangement adjustable, it is possible in the back focal plan of X-ray objective 8, a segmented phase ring 20. This arrangement is shown in FIG. 3a. The segmented phase ring (20) comprises many phase-shifting and non-phase-shifting segments 26, 27. The segments 26, 27 are preferably all of the same size and are distributed equidistantly over the region of the phase ring 20 (FIG. 2c). If an annular condenser zone plate as shown in FIG. 3 is used, a phase contrast image and an amplitude contrast image are then generated simultaneously on the detector. If a rotating condenser 13 as shown in FIG. 4 is used, a phase contrast image and an amplitude contrast image are then generated alternatingly in the image plane during the rotational movement, and are recorded in the image plane sequentially by detector 9, 12.

Figure 4:
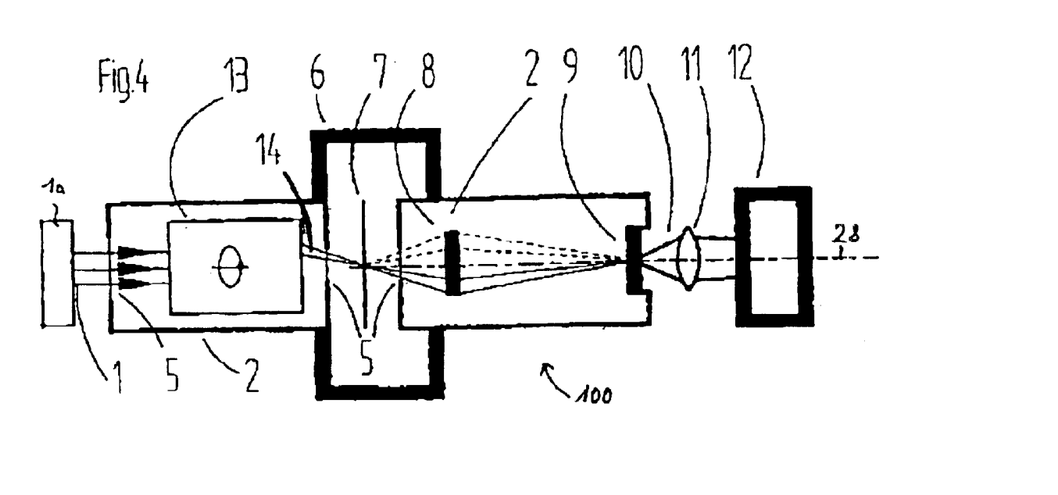
FIG. 4 shows an X-ray microscope in which an X-ray objective creates a real image of the specimen being examined.

If, as an improvement to X-ray microscope 100 as shown in FIGS. 3 and 4, a stop 29 (FIG. 2d) made of transparent segments 23 and absorbent segments 22, corresponding in appearance to the segmented phase ring shown in FIG. 2c, is arranged in front of or behind the plane of condenser optical system 3 (FIG. 3) or that of rotating condenser 13 (FIG. 4), it is then possible to ensure, by appropriate rotation of the stop shown in FIG. 2d or of the phase ring shown in FIG. 2c about optical axis 28 into one position or the other, that X-ray light of zero diffraction order from specimen 7 passes either only through transparent region 27 of the segmented phase ring or only through phase-shifting region 26. In phase contrast mode, stop 29 (FIG. 2d) and phase ring 20 (FIG. 2c) are positioned with respect to one another so that the zero-order light from specimen 7 through segments 23 falls only through phase-shifting segments 26 of the phase ring; in amplitude contrast, the zero-order radiation falls only into segments 27.

As a further improvement, segmented stop 29 can be eliminated by using as X-ray condenser 3 an annular condenser zone plate 19 as shown in FIG. 2b, structured only with segments 25 with zone sections and zone-free segments 24, corresponding to the phase ring. When condenser zone plate 19 (FIG. 2b) segmented in this fashion, or segmented phase ring 20 (FIG. 2c), is then rotated appropriately, it is thus possible to switch over from imaging in phase contrast to imaging in amplitude contrast: in phase contrast, condenser 3 is positioned so that the zero-order light from specimen 7 passes only through phase-shifting segments 26 of phase ring 20, whereas in amplitude contrast, the zero-order radiation falls only between them, into segments 27.

As a further improvement, the specimen plane illuminated in so-called "critical illumination" can be illuminated more homogeneously by scanning condenser zone plate 3 two-dimensionally over the specimen field using positioning elements.

In order to record a pure phase contrast or amplitude contrast image in X-ray microscope 100 as shown in FIG. 4 using a rotating condenser 13, a chopper disk having at least one transmitting segment can be mounted along the beam path. The chopper disk is synchronized with the rotational movement of rotating condenser 13. Depending on the phase angle between the chopper disk and rotating condenser 13, recording of the phase contrast image or amplitude contrast image on detector 9, 12 is permitted by the fact that the radiation that would result in generation of the undesired image contrast is allowed to fall on the chopper disk and is thereby blocked out. This can also be accomplished outside the X-radiation beam path if a mechanical or electro-optical shutter is placed between X-ray converter 9 and camera 12; or if camera 12 activates recording, via electronic actions, only during the periods in which the image that is intended to be recorded is present.

Instead of the arrangement of a phase plate or phase ring as shown in FIG. 2c with a support film, it is possible to structure these phase-shifting elements in a cantilevered fashion. With a cantilevered structure, the segments are held at the rim by a series of fine support struts, perhaps of spoke-like or statistically distributed configuration, which join the segments to one another and to an outer retaining ring.

Two optical systems are required in imaging X-ray microscope 100 shown in FIG. 3: a condenser optical system 3 that focuses incident X-radiation 1 onto specimen 7 that is being examined; and an X-ray objective 8 that captures the X-radiation that has penetrated through specimen 7. X-ray objective 8 generates a real image of specimen 7 on a spatially resolving detector device that, after an image integration delay, outputs an image signal to a monitor.

As already mentioned, the spatially resolving detector device in imaging microscope 100 comprises X-ray converter 9, lens 11, and camera 12. Camera 12 records the image. Because of the possibility of damage to camera 12 if it is irradiated with X-rays of very short wavelengths, however, it is best if visible radiation is first generated from the real X-ray image. For example, it is possible to use a fluorescing substance of X-ray converter 9, such as phosphor. Visible radiation 10 is then imaged onto camera 12 for visible light, for example a CCD detector, using an optical system 11 that, can contain a deflecting mirror so as to remove camera 12 from the direct X-ray beam and thus eliminate any possible X-radiation damage. Such radiation damage to the CCD detector occurs when X-rays of wavelengths less than 2 nm are used, since this X-radiation can penetrate into X-ray CCD image sensors, with perceptible transmittance, to a depth of several micrometers. This is the depth, however, at which the electrical conductor paths, insulating layers, and semiconducting functional elements of a CCD image sensor are located, and continuous irradiation with relatively high-energy X-radiation can permanently damage them, for example, by disrupting and/or destroying the insulating layers between the conductor paths. Instead of X-ray converter 9, however, it is also possible to arrange, directly in X-ray microscope 100, a camera having a PN-CCD which is insensitive to radiation damage.

If an imaging X-ray microscope 100 of this kind is operated in phase contrast, a phase plate in the back focal plane of the X-ray objective should be arranged. For an imaging X-ray microscope 100, this phase plate is usually configured annularly, i.e. as a phase ring. When zone plates 18 are used as X-ray objective 8, it is always necessary to illuminate specimen 7 with a hollow-cone beam, to prevent the image in the central region from being overlaid with radiation containing no information, which can consist of zero-order radiation of zone plate 18 (micro-zone plate).

In practice, therefore, a condenser 3 that casts no light from its center onto the specimen is always selected. This can be achieved, for example, with an annular condenser zone plate 19, or the central radiation can be blocked out by means of a stop 4 after the condenser optical system. It is possible, as depicted in FIG. 4, that an imaging X-ray microscope 100 can contain as the condenser optical system a rotating condenser 13 from which radiation 14 shines obliquely onto specimen 7. Rotation of condenser 13 then generates the necessary hollow-cone illumination for specimen 7. The rest of the configuration corresponds to that of FIG. 3.

Rotating condenser 13 can also contain rotating mirrors that are coated with multilayer coatings. For a limited wavelength region and for the angles of incidence that can be greater than the limit angle for total reflection, multilayer coatings of this kind still possess a high reflectivity that is typically well above 10%.

It is thereby possible to work, at wavelengths below 1 nm, with angles of reflection that are typically 10 times greater than the angles of incidence at which simple mirrors, exploiting total reflection, can be used. Typical angles of incidence of 1° can be achieved for multilayer mirrors. Since much shorter mirror lengths are thereby sufficient to achieve a required projected area of the mirror in a plane perpendicular to optical axis 28 of X-ray microscope 100, the use of multilayer mirrors simplifies the design of a rotating condenser 13, since the required mirror lengths are short. Angular alignment of the mirrors is also simpler, since the absolute angular tolerances that must be adhered to are much greater than when simple mirrors are used for total reflection.

Figure 5:
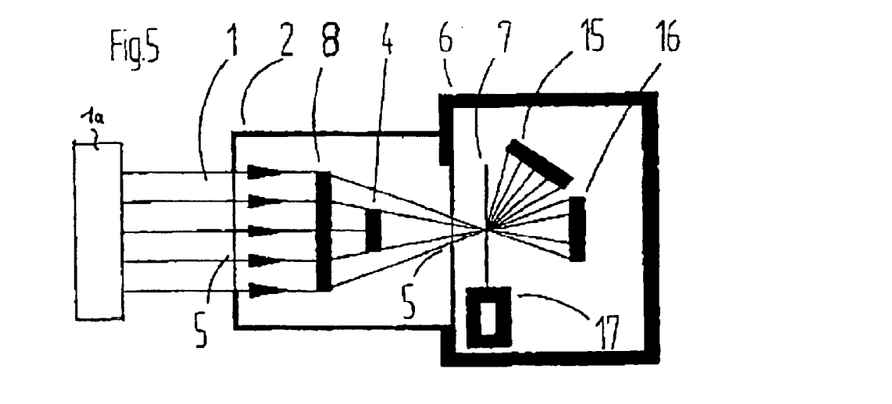
FIG. 5 shows a scanning X-ray microscope that passes radiation through the specimen.

In scanning X-ray microscopes as shown in FIG. 5, an X-ray objective 8 is illuminated by an X-ray wave 1. X-ray objective 8 focuses X-ray wave 1, in the plane of specimen 7, to a small X-ray light spot. The X-ray light passing through specimen 7 is measured with an X-ray detector 16, with or without spatial resolution. Specimen 7 is moved in a scanning motion by means of a scanning mechanism 17 that contains translators. These can contain piezoelectric elements, pneumatics, plunger coils, mechanical spindles, levers, or other displacement devices. Detector 16 records the X-ray light penetrating through specimen 7. The image is built up point by point on a monitor, i.e. serially. Scanning is usually accomplished either by moving specimen 7 two-dimensionally or by moving X-ray objective 8 two-dimensionally, or by moving both elements in mutually perpendicular directions. Additionally located behind X-ray objective 8 is an X-ray absorbing stop 4 creating a shadow where the X-ray light spot is generated.

If a scanning X-ray microscope is to be operated in phase contrast, it is necessary to mount, in front of an annular portion of X-ray objective 8, an annular phase plate which appropriately rotates the X-ray wave that impinges upon it. The annular phase plate is made of a material having a suitable optical constant, which is mounted on a film transparent to X-rays and which is aligned concentrically with X-ray objective 8.

A further possibility for scanning phase contrast X-ray microscopy is created if an entirely normal X-ray objective is used instead of a phase ring, and if an extended detector with a segmented surface, whose segments can be read out individually, is used to obtain the phase information. The phase information is then obtained by combining the individual signals of the segments, for example by differentiating the signals of opposite segments.

When a scanning X-ray microscope is operated with high-energy radiation, it is possible to generate X-ray fluoresceuce radiation from all those chemical elements that have absorption discontinuities with energies lower than that of the exciting radiation. Detector 15 for X-ray fluorescence is shown in FIG. 5. A scanned transmission image and a fluorescence image can thus be recorded simultaneously.

What is claimed is:

1. A method for examining structures on a semiconductor substrate that has a thickness, the method comprising:

obtaining integrated circuits as structures on the semiconductor substrate, wherein the structures on the semiconductor substrate are passivated;

penetrating and imaging the structures with X-radiation in an imaging X-ray microscope onto a spatially resolving detector; and establishing of a wavelength or a wavelength region of the X-radiation as a function of the thickness of the semiconductor substrate in such a way chat transmission of the X-radiation through the semiconductor substrate is at least sufficient for detection of the X-radiation and for obtaining a high contrast image; and observing changes in distribution of a material of the structures corresponding to a change of contrast of the high contrast image.

2. The method as defined in claim 1, further comprising reducing the thickness of the semiconductor substrate without affecting the structures.

3. The method as defined in claim 1, wherein the semiconductor substrate is made of silicon, the substrate thickness is less than 30μm, and the X-radiation has a wavelength between 0.1 nm and 2 nm.

4. The method as defined in claim 1, wherein the wavelength of the X-radiation is selected in accordance with Rayleigh-Gans algorithms for scattering to provide an optimum X-ray optical scattering capability for the structures on the substrate in order to obtain the high-contrast image with a high signal-to-noise ratio.

5. The method as defined in claim 1, wherein the wavelength of the X-radiation selected for examination of metal structures on the substrate is in a vicinity of corresponding absorption discontinuities of the metals, resulting in the high image contrast.

6. The method as defined in claim 1, wherein the X-radiation impinges upon the semiconductor substrate at a side containing no structures.

7. The method as defined in claim 1, wherein the structure are imaged at different observation angles in order to allow stereographic and tomographic reconstructions.

8. The method as defined in claim 1, wherein the X-ray microscope is operating in phase contrast to provide a minimum number of photons and minimal exposure time for obtaining an image.

9. The method as defined in claim 1, wherein a segmented phase plate is used in a back focal plane of an X-ray objective.

10. The method as defined in claim 9, wherein a segmented stop disposed between an X-ray source and a condenser of the X-ray microscope is used.

11. The method of claim 10, wherein a segmented annular condenser zone plate, or a rotating condenser having a chopper disk, is used as the condenser.

12. An imaging X-ray microscope for examining structures on a semiconductor substrate having a thickness, the X-radiation microscope comprising:

a specimen chamber for examining a specimen, wherein the specimen is an integrated circuit with the structures formed on the semiconductor substrate and wherein the structures are passivated;

an objective for imaging the structures with X-radiation on a spatially resolving detector; and an X-radiation source generating the X-radiation having a wavelength which is a function of the thickness of the semiconductor substrate, wherein transmission of the X-radiation through the semiconductor substrate is at least sufficient for detection of the X-radiation, and for obtaining a high-contrast image to observe changes in distribution of a material of the structures corresponding to a change of contrast of the high contrast image.

13. The imaging X-ray microscope as defined in claim 12, wherein a segmented phase plate is disposed in a back focal plane of the X-ray objective.

14. The imaging X-ray microscope as defined in claim 13, wherein a segmented stop is disposed between the X-radiation source and a condenser of the X-ray microscope.

15. The imaging X-ray microscope as defined in claim 14, wherein a segmented annular condenser zone plate or a rotating condenser having a chopper disk is provided as the condenser.

* * * * *